United States Patent [19]
Brodsky

[11] Patent Number: 5,351,675
[45] Date of Patent: Oct. 4, 1994

[54] METHOD AND APPARATUS FOR PREHEATING AN OPTICAL INSTRUMENT PRIOR TO USE THEREOF IN A MEDICAL PROCEDURE

[75] Inventor: David L. Brodsky, Providence, R.I.

[73] Assignee: The Kendall Company, Mansfield, Mass.

[21] Appl. No.: 929,825

[22] Filed: Aug. 14, 1992

[51] Int. Cl.$^5$ ............................ A61B 1/00; F24J 1/00
[52] U.S. Cl. ...................................... 128/4; 126/263
[58] Field of Search ............... 604/291, 113; 206/219, 206/438; 126/263; 128/4, 6

[56] References Cited

U.S. PATENT DOCUMENTS

| | | | |
|---|---|---|---|
| 3,685,507 | 8/1972 | Donnelly | 126/263 |
| 4,057,047 | 11/1977 | Gossett | 126/263 |
| 4,838,242 | 6/1989 | Oblon | 126/263 |
| 5,101,804 | 4/1992 | Cohn | 126/263 |
| 5,137,011 | 8/1992 | Roth | 126/263 |
| 5,163,504 | 11/1992 | Resnick | 126/263 X |
| 5,172,683 | 12/1992 | West | 126/263 |
| 5,207,213 | 5/1993 | Auhill et al. | 128/6 |

Primary Examiner—Richard J. Apley
Assistant Examiner—Karen A. Jalbert
Attorney, Agent, or Firm—Alvin Isaacs

[57] ABSTRACT

A method and apparatus for preheating an optical instrument prior to use thereof in a medical procedure, wherein the optical instrument includes an elongated optical shaft portion. The apparatus includes a casing for receiving the optical shaft portion therein and a heater mechanism in the casing for heating the shaft portion. The method includes the steps of assembling the shaft portion in the casing and leaving it therein until the shaft portion has been heated to at least the normal body temperature of a patient.

11 Claims, 1 Drawing Sheet

METHOD AND APPARATUS FOR PREHEATING AN OPTICAL INSTRUMENT PRIOR TO USE THEREOF IN A MEDICAL PROCEDURE

BACKGROUND AND SUMMARY OF THE INVENTION

The instant invention relates to optical instruments for use in medical procedures and more particularly to a method and apparatus for preheating an optical instrument, such as a laparoscope, prior to use thereof in a medical procedure.

A number of relatively sophisticated fiberoptic instruments have been developed for use in medical procedures in recent years. These instruments, which have included laparoscopes and endoscopes, have become increasingly important in an increasingly wide range of medical procedures. Further, it has been found that many medical procedures which have previously required highly traumatic invasive surgery can now be performed without conventional surgery utilizing specially adapted optical devices. Consequently, it has been found that many medical conditions can now be treated in new procedures which result in substantially reduced levels of trauma to patients.

It has been found that one particular problem which is frequently encountered when performing medical procedures on patients utilizing optical instruments, such as those which include fiberoptic components contained in elongated shaft portions, is that moisture often tends to condense on the optical components of such instruments during the initial stages of medical procedures. Obviously, this interferes with the ability of physicians to clearly view the areas of patients under consideration. Further, while various attempts have been made to remedy this problem by providing antifog lenses for and sealing the optical components of such instruments it has been found that fogging nevertheless persists as a significant and troublesome problem.

In connection with the above it has been found that the main reason for instrument fogging is that optical instruments which are used in medical procedures are normally maintained at room temperature prior to use. Accordingly, when they are initially exposed to the inherently warm moist conditions which exist in the bodies of patients they tend to cause moisture to condense on the various components of the instruments, including the optical components thereof. As a result, when portions of optical instruments of this type are initially passed into the bodies of patients it is normally necessary to wait several minutes for the condensation which is likely to form on the instruments to dissipate before medical procedures can be performed.

The instant invention provides a method and apparatus which can be utilized for overcoming the problem of forming condensation on an optical instrument during the initial periods of use thereof in a medical procedure on a patient. Specifically, the instant invention provides a method and apparatus for preparing an optical instrument for use in a medical procedure on a patient. More specifically, the apparatus of the instant invention comprises a casing which is adapted for receiving the shaft portion of an optical instrument therein and heater means in the casing for heating the shaft portion to a temperature which is at least equal to the normal body temperature of a patient. The heater means preferably comprises means which is actuatable for producing an exothermic chemical reaction in order to heat the instrument. Specifically, the means for producing an exothermic chemical reaction preferably comprises of flexible bag in the casing containing a first chemical and a rupturable member containing a second chemical. The rupturable member is rupturable for introducing the second chemical into the first chemical in order to produce an exothermic chemical reaction, and it is rupturable from the exterior of the casing. The first and second chemicals preferably comprise water and magnesium sulfate, respectively, and the casing preferably comprises a elongated sheath having an open end for receiving the shaft portion of an instrument therein.

Accordingly, the method of using the apparatus of the instant invention comprises assembling the elongated optical shaft portion of an optical instrument in a preheating device comprising a casing which is adapted for receiving the shaft portion therein and means in the casing for heating the shaft portion, and leaving the shaft portion in the casing until it has reached a temperature which is at least approximately equal to the normal body temperature of a patient. When the means for heating the instrument in the casing comprises first and second chemicals which are adapted to be mixed together to form an exothermic reaction the method preferably further comprises mixing the chemicals together by rupturing the rupturable means so as to produce an exothermic reaction. When the instrument comprises a laparoscope the method preferably comprises assembling substantially the entire shaft portion of the laparoscope in the sheath, and leaving the shaft portion therein until the shaft portion has reached a temperature which is at least approximately equal to the normal body temperature of a patient.

It has been found that the method and apparatus of the instant invention can be effectively utilized for heating an optical instrument prior to use thereof in a medical procedure on a patient so that the instrument is not prone to forming condensation thereon when it is initially introduced into the body of the patient. Specifically, it has been found that the method and apparatus of the instant invention can be effectively utilized for preheating an optical instrument, such as a laparoscope, so that the fiberoptic and lens portions of the instrument are not prone to developing condensation thereon during the initial stages of a medical procedure. It has been further found that by providing an effective sheath type casing containing chemicals which are capable of producing an exothermic chemical reaction the shaft portion of a medical optical instrument can be effectively preheated prior to the insertion thereof into the body of a patient, whereby the lens components of the instrument are not prone to forming condensation.

Accordingly, it is a primary object of the instant invention to provide an effective method of preparing an optical surgical instrument for use prior to the insertion thereof into the body of a patient.

Another object to the instant invention is to provide an effective method of preheating an optical instrument, such as a laparoscope.

An even further object of the instant invention is to provide an effective apparatus for preheating an optical instrument prior to use thereof in a medical procedure.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
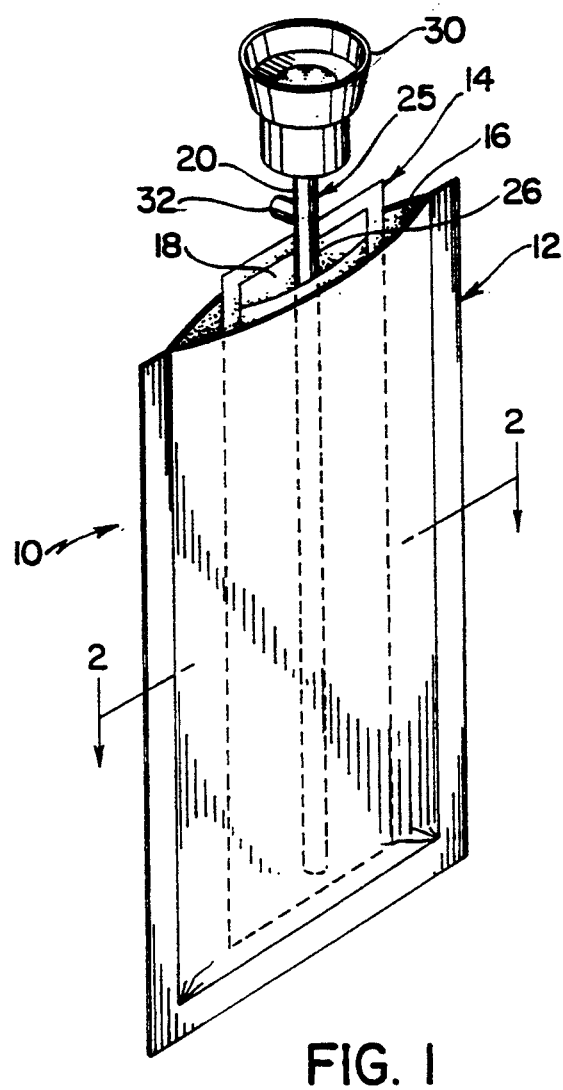
FIG. 1 is a perspective view of the apparatus of the instant invention with the shaft portion of a laparoscope received therein.
Figure 2:
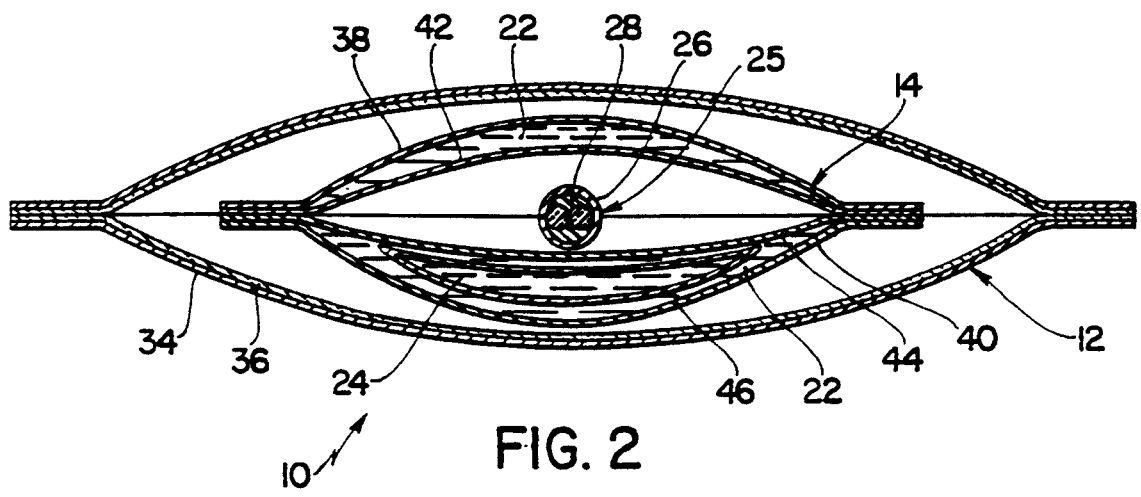
FIG. 2 is a cross sectional view taken along line 2—2 in FIG. 1.

Referring now to the drawings, the apparatus of the instant invention is illustrated in FIGS. 1 and 2 and generally indicated at 10. The apparatus 10, which is operative in accordance with the method of the subject invention, comprises an outer casing generally indicated at 12 and an inner sleeve assembly generally indicated at 14. The outer casing 12 comprises an insulated outer casing of elongated configuration having an open end 16, and the inner sleeve assembly 14 is also of elongated configuration, and it is adapted to be received in the casing 12. The inner sleeve assembly 14 has an open end 18, and it is adapted for receiving an optical instrument of a type which is adapted for use in a medical procedure, such as a laparoscope 20, therein as illustrated in FIG. 1. Further, the inner assembly sleeve 14 includes first and second chemicals 22 and 24, respectively which are mixable for producing and exothermic chemical reaction in order to heat the laparoscope 20 when it is received in the sleeve assembly 14.

While the heating apparatus of the subject invention can be effectively adapted for use in combination with a variety of different medical instruments the apparatus 10 as herein embodied is illustrated in combination with the laparoscope 20. In this regard, the laparoscope 20, as herein illustrated, is of conventional construction, and it comprises an elongated shaft portion 25 comprising an outer casing layer 26 and an internal assembly 28 which is of conventional construction and preferably comprises one or more fiberoptic components. The laparoscope 20 further comprises an eyepiece and lens assembly 30 at one end thereof and a camera connection 32 adjacent the eyepiece and lens assembly 30.

The outer casing 12 is operative for thermally insulating the inner sleeve assembly 14 and, as herein embodied, it comprises an outer shell 34 which may be made of a suitable material, such as a heavy paper, and an inner insulative layer 36 which preferably comprises a thermally insulative synthetic foam material. It will be understood, however, that various other embodiments of the outer casing 12, which are constructed of various other materials, but which are nevertheless adapted for thermally insulating the inner sleeve assembly 14, are contemplated.

The inner sleeve assembly 14 comprises a plurality of layers of a suitable plastic material, such as polypropylene, which cooperate to define a series of compartments in the sleeve assembly 14. In this regard, the sleeve assembly 14, as herein embodied, comprises first and second flexible plastic outer layers 38 and 40 which are sealed to each other along opposite longitudinal side edges and a bottom edge, so that they cooperate to define an open ended bag-like structure. The sleeve assembly 14 further comprises first and second inner layers 42 and 44 which are sealed to the outer layers 38 and 40 along the longitudinal side edges thereof but not along the bottom end of the bag-like structure formed by the outer layers 38 and 40. The inner layers 42 and 44 are, however, sealed to each other at a bottom end edge which is spaced inwardly from the bottom end edge defined by the outer layers 38 and 40. Accordingly, the outer layers 38 and 40 and the inner layers 42 and 44 cooperate to define a cavity therebetween for containing the first chemical 22. Further, because the bottom end edges of the inner layers 42 and 44 are sealed to each other in spaced relation to the bottom end edges of the outer layers 38 and 40 opposite side portions of the cavities formed by the layers 38, 40, 42, and 44 are in fluid communication with each other. Also included in the sleeve assembly 14 is a rupturable inner envelope 46 which is disposed between the layers 44 and 40 in the first chemical 22. The inner envelop 46 is operative for containing the second chemical 24, and it is adapted so that it is rupturable, such as by squeezing it from the exterior of the apparatus 10, in order to release the second chemical 24 into the first chemical 22. Obviously, other embodiments of the envelope 46, such as embodiments which include one or more ridged rupturable vials or the like, are contemplated, the important feature being that the envelope 46 is rupturable to release the second chemical 24 into the first chemical 22 when desired.

The first and second chemicals 22 and 24 preferably comprise liquid chemicals which are operative for spontaneously producing a controlled exothermic chemical reaction when they are mixed together. The first chemical 22 preferably comprises water and the second chemical 24 preferably comprises magnesium sulphate which is mixable with the water 22 to spontaneously produce a controlled exothermic chemical reaction. In this regard, while obviously it is important that the reaction produced by the chemicals 22 and 24 does not produce sufficient heat to melt the layers 38, 40, 42, and 44, it must nevertheless produce a sufficient amount of heat to raise the temperature of the shaft portion 25 to a level which is at least equal to the normal body temperature of a patient.

Accordingly, for use and operation of the apparatus 10 the rupturable membrane 46 is ruptured to release the second chemical 24 into the first chemical 22 in order to produce a spontaneous exothermic chemical reaction. The laparoscope 20 is then installed in the inner compartment defined by the layers 42 and 44 so that the shaft portion 25 can absorb sufficient heat from the chemicals 22 and 24 to elevate the temperature thereof to a level which is at least equal to the normal body temperature of a patient. Obviously, however, it is not desirable to heat the shaft portion 25 to a level which would cause it to have harmful effects on the patient. Once the shaft portion 25 has been adequately heated in this manner the laparoscope 20 can then be utilized in a medical procedure for observing certain selected areas in the interior of the body of the patient without being hampered by the formation of condensation on the laparoscope 20.

It is seen therefore that the instant invention provides an effective method and apparatus for preparing an optical instrument for use in a medical procedure in which a shaft portion of the instrument is inserted into the body of a patient. The apparatus 10 is effectively operative for preheating the shaft portion 25 so that the laparoscope 20 is not normally subject to the formation of condensation thereon. Specifically, the chemicals 22 and 24 are mixable to produce an exothermic chemical reaction, whereby the shaft portion 25 can be effectively heated in the inner sleeve assembly 14 without causing the shaft portion 25 to contact the chemicals 22 and 24. Consequently the laparoscope 20 can be effectively utilized in a medical procedure without developing condensation thereon which would interfere with the vision of a surgeon performing the procedure. Hence it is seen that the method and apparatus of the subject invention represent significant advancements in the medical art which have substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. In combination, a laparoscope and an apparatus for preheating said laparoscope prior to use thereof in a medical procedure, said laparoscope including an elongated optical shaft portion which is adapted to be received in the body of a patient, said apparatus comprising an elongated sleeve dimensioned for receiving said shaft portion therein, said sleeve having an open end and a closed end and including flexible inner and outer walls which cooperate to define a compartment therebetween, said inner wall defining an inner pocket dimensioned for receiving said laparoscope therein, said pocket having an open end and a closed end which correspond to the open and closed ends of said sleeve, respectively, said compartment substantially completely surrounding said pocket, and heating means in said compartment for heating said shaft portion.

2. In the combination of claim 1, said means for heating said laparoscope comprising means actuatable for producing an exothermic chemical reaction in said compartment in order to heat said instrument in said sleeve.

3. In the combination of claim 2, said means for producing an exothermic chemical reaction comprising a first chemical in said compartment, and rupturable means containing a second chemical, said rupturable means being rupturable for introducing said second chemical into said first chemical, said first and second chemicals reacting in an exothermic chemical reaction upon mixing thereof together, said rupturable means being rupturable by manipulating said sleeve from the exterior thereof to cause said first and second chemicals to become mixed together.

4. In the combination of claim 3, said first and second chemicals comprising water and magnesium sulfate, respectively.

5. In the combination of claim 1, said inner wall comprising first and second substantially flat inner wall sections which are secured together in substantially face to face overlying relation so that they cooperate to define said pocket in a substantially flat elongated configuration.

6. In the combination of claim 5, said first and second inner wall sections each having a pair of spaced longitudinally extending side edges, said first and second wall sections being secured to each other along the side edges thereof.

7. In the combination of claim 6, said first and second inner wall sections each having a pair of opposite end edges, said first and second inner wall sections being secured together along one end edge of each of said first and second inner wall sections, the opposite end edges of said inner wall sections defining said open end.

8. The combination of claim 1 further comprising an outer casing, said sleeve being received in said outer casing, said outer casing having an opening, said open end of said sleeve being aligned with said opening in said outer casing.

9. In the combination of claim 1, said heating means extending substantially throughout said compartment.

10. A method of preventing fogging of an optical instrument used in a medical procedure on a patient, said instrument including an elongated optical shaft portion, said method comprising assembling said instrument in a preheating device including a casing for receiving at least a portion of said instrument shaft portion therein and means for heating said instrument shaft portion in said casing, and leaving said instrument shaft portion in said cashing until it has reached at least approximately the normal body temperature of said patient, said means for heating said instrument in said casing comprising first and second chemicals which are mixable to form an exothermic reaction, said method further comprising mixing said chemicals to produce an exothermic chemical reaction.

11. In the method of claim 10, said instrument comprising a laparoscope having an elongated optical shaft portion and an optical lens on said shaft portion, said casing being dimensioned for receiving substantially said entire shaft portion therein, said assembling step comprising assembling substantially said entire shaft portion in said casing.

* * * * *